United States Patent [19]

Feppon et al.

[11] Patent Number: 4,925,310
[45] Date of Patent: May 15, 1990

[54] METHOD AND DEVICE TO MEASURE THE OPTICAL TRANSMISSION FACTOR OF A TINTED GLASS PANEL BY REFLECTION

[75] Inventors: Philippe Feppon, Annecy; Charles Rydel, Paris, both of France

[73] Assignee: Jaeger, Levallois-Perret, France

[21] Appl. No.: 180,823

[22] Filed: Apr. 12, 1988

[30] Foreign Application Priority Data

Apr. 14, 1987 [FR] France .................. 87 05272

[51] Int. Cl.⁵ .................. G01J 1/10; F21M 3/00
[52] U.S. Cl. .................. 356/434; 250/341
[58] Field of Search .............. 356/381, 382, 432, 433, 356/434, 443; 250/341

[56] References Cited

U.S. PATENT DOCUMENTS

| 1,848,874 | 3/1932 | Fitzgerald | 356/432 |
| 3,589,814 | 6/1971 | Patterson | 356/434 |
| 4,015,127 | 3/1977 | Sharkins | 250/341 |
| 4,125,328 | 11/1978 | Suga | 356/124 |
| 4,167,335 | 9/1979 | Williams | 356/336 |

FOREIGN PATENT DOCUMENTS 3345897 7/1985 Fed. Rep. of Germany.

Primary Examiner—Richard A. Rosenberger

[57] ABSTRACT

In a method and a device for determining the optical transmission factor of a glass panel by identification transmits an incident electromagnetic radiation towards the glass panel and the intensity of the reflected radiation is detected and measured. The reflection coefficient of the panel is compared with reflection coefficient reference values representing the transmission factor of tinted glass reference panels to determine the optical transmission factor of the panel examined.

12 Claims, 2 Drawing Sheets

METHOD AND DEVICE TO MEASURE THE OPTICAL TRANSMISSION FACTOR OF A TINTED GLASS PANEL BY REFLECTION

BACKGROUND OF THE INVENTION

1. Field of the Invention

The present invention relates to a method and device to measure the optical transmission factor of a tinted glass panel by reflection.

2. Description of the Prior Art

Usually, the optical transmission factor of a glass panel is ascertained by direct measurement of the ratio between the flux of an electromagnetic radiation transmitted by this panel and the flux of the incident electromagnetic radiation that creates it.

However, for this purpose, the incident electromagnetic radiation transmitters and the receivers for the transmitted electromagnetic radiation should be placed on either side of the glass panel to be examined. These standard systems cannot easily be used if the glass panel is a wall between two environments, with one environment subjected to adverse weather and/or severe ambient conditions while the other environment is a shielded environment or chamber. This is the case, for example, when the glass panel forms the windshield of a motor vehicle or an aircraft: the optical transmission factor of this glass panel has to be determined regularly to ensure the optimal functioning of accessory driving or piloting equipment (for example fog detectors or similar instruments) calling for a precise knowledge of the transmission factor of the glass panel. For these standard systems entail the installation of the receivers in the external environment or subjecting them to severe environmental conditions and this, of course, considerably increases the cost of their use.

An object of the present invention is to remove the above-mentioned drawbacks by implementing a method and device to determine the optical transmission factor of a glass panel by reflection.

Another object of this invention is the implementation of a method and a device to determine the transmission factor of a glass panel by reflection, wherein all the equipment used is located on one and the same side of the glass panel, in the shielded environment.

Another object of the present invention is the implementation of a method and a device making it possible, when changing the glass panel that forms the windshield of a motor vehicle or an aircraft, to directly determine the transmission factor of this glass panel by reflection, in order to provide for the corresponding control of accessories of the vehicle or the aircraft, the functioning of which depends on the value of the above-mentioned factor.

Another object of the invention is also the implementation of a method and device which can be used, when there exists a glass panel with a shade and/or opacity variable according to ambient luminosity, to make a corresponding check on accessories of the vehicle or aircraft, the functioning of which depends on the value of the above-mentioned transmission factor depending on the tint and/or opacity of said panel.

SUMMARY OF THE INVENTION

A distinguishing feature of the method, according to the present invention, for determining the optical transmission factor of a tinted glass panel by reflection, is that it consists in transmitting an incident electromagnetic radiation towards the tinted glass panel, detecting and measuring the amplitude of the electromagnetic radiation reflected by the tinted glass panel, and then comparing the amplitude of the reflected electromagnetic radiation with several reflection coefficient reference values representing the transmission factor of the tinted glass panel.

A distinguishing feature of the device to implement the above-mentioned method of the invention is that it comprises means for transmitting an electromagnetic radiation of a determined wavelength towards the glass panel, means for the reception of the electromagnetic radiation reflected by the glass panel, said reception means delivering a signal of an amplitude representing the amplitude of the electromagnetic radiation reflected by the glass panel, and means to compare the signal representing the electromagnetic radiation reflected by the glass panel with reflection coefficient reference threshold values representing the transmission factor of the glass panel.

BRIEF DESCRIPTION OF THE DRAWINGS

The method and device of the invention will be better understood from the following description and the appended drawings, of which.

DESCRIPTION OF THE PREFERRED EMBODIMENT

Figure 1A:
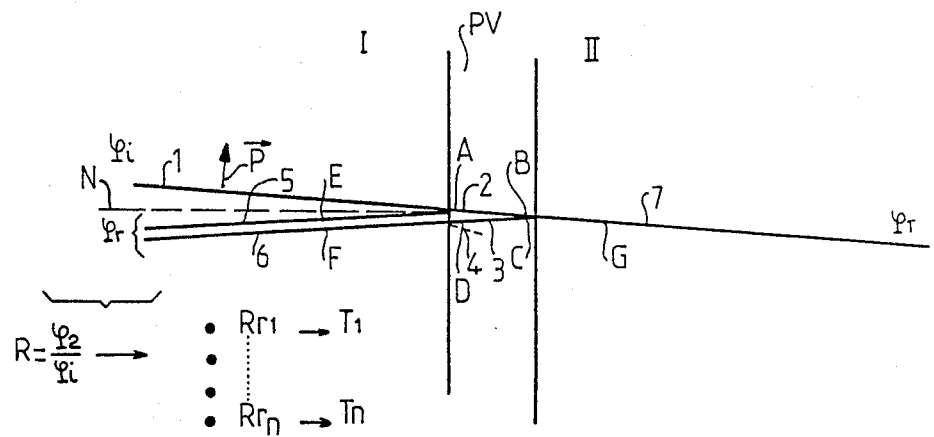
FIG. 1a is a drawing illustrating the implementation of the method of the invention.

The method of the invention for determining the optical transmission factor of a tinted glass panel by reflection shall be described first of all in relation to FIG. 1a.

According to the above-mentioned figure, the method of the invention consists in transmitting an incident electromagnetic radiation of given intensity towards the tinted glass panel marked PV. In FIG. 1a, the intensity of the incident radiation is marked $\phi_i$ and the incident radiation is marked 1. The method of the invention also consists in detecting and measuring the intensity, marked $\phi_r$, of the electromagnetic radiation reflected by the tinted glass panel PV. FIG. 1a shows the incident radiation 1. This radiation is partially refracted into a radiation 2 in the glass panel PV, this same incident radiation 1 being partially reflected in a first reflected radiation marked 5, this reflection acting on the inlet diopter of the glass panel PV, said diopter separating the environment marked I or first environment, forming the shielded environment for example, and the constituent material of the glass panel PV. The refracted radiation 2 is itself subjected to a further refraction on the second diopter separating the glass panel PV from the second environment, marked II, to give rise to the transmitted radiation or emergent radiation, marked 7, with an intensity $\phi_T$. The first radiation 2 refracted in the glass panel PV also gives rise to a refracted radiation marked 3, which is itself refracted by the first diopter, separating the glass panel PV from the first environment marked I, to give rise to a second reflected radiation marked 6. Of course, successive reflections of radiations reflected by the second diopter and then the first diopter, such as the radiation 4 and other successive radiations may be revealed. However, for perfectly justified reasons, the intensity of these successive reflected radiations can be overlooked. Thus, the reflected electromagnetic radiation, with an intensity $\phi_r$, essentially consists of above-described reflected radiations 5 and 6. It thus constitutes the electromagnetic radiation reflected by the tinted glass panel PV with an intensity $\phi_r$.

For an angle of incidence of the incident radiation with an intensity $\phi_i$, the radiation 1, and for the two diopters separating the glass panel PV from the environments I and II, the reflection coefficients k of the first and second diopters, are substantially identical for the incidence considered.

According to one aspect of the method of the invention, it has been observed that, when glass panels PV of the same nature, such as for example laminated glass windshields for motor vehicles, are tinted differently, they have a refraction index n which is substantially identical regardless of the shade of the glass panel PV considered. Consequently, the reflection coefficient k of the inlet and outlet diopters is substantially constant according to the shade and generally below 10%. On the contrary, the transmission factor T and the absorption coefficient for each of the shades considered appear to be very different depending on the above-mentioned shades.

Thus, for the points A, B, located on the electromagnetic radiation 2, respectively in the vicinity of the inlet diopter and the outlet diopter of the glass panel PV and inside it, for the points C, D located on the electromagnetic radiation 3 in the vicinity of the points B and A respectively, for the points E and F respectively located on the electromagnetic radiation 5 and 6, and for a point G located on the emergent radiation 7, it is possible to write the following relationships successively, giving the corresponding intensities as a function of the incident intensity $\phi_i$:

$$pt\ A: (1 - k)\phi i$$
$$pt\ B: (1 - k)(1 - a)\phi i$$
$$pt\ C: k(1 - k)(1 - a)\phi i$$
$$pt\ D: k(1 - k)(1 - a)^2 \phi i$$
$$\left.\begin{array}{l} pt\ E: k\ \phi i \\ pt\ F: k(1 - k)^2 (1 - a)^2 \phi i \end{array}\right\} = R\ \phi i$$
$$pt\ G: (1 - k)^2 (1 - a)\phi i = T\phi i$$

From the preceding relationships, we can deduce the relationship linking the reflection coefficient R of the glass panel PV to its transmission factor T as a function of the reflection coefficient k of the inlet and outlet diopters:

$$R = k\left[1 + \frac{T^2}{(1 - k)^2}\right]$$

It will be noted that, for a glass panel, illuminated by an incident radiation at substantially normal incidence, the reflection coefficient k of the inlet and outlet diopters is far smaller than 1 and is close to 4%. Thus, when there is a change in shade of the glass panel PV, k remains substantially constant, and the reflection coefficient R of the glass panel PV thus represents its optical transmission factor T.

As represented schematically in FIG. 1a, the method of the invention thus consists in comparing the ratio $R = \phi_r/\phi_i$ between the intensity of the reflected electromagnetic radiation and the intensity of the incident electromagnetic radiation, this ratio representing the reflection coefficient R of the glass panel PV, with several reflection coefficient reference values marked $R_{rl}...R_{rn}$. Each reflection coefficient reference value is uniquely related to the transmission factor as demonstrated by the above formula and reference limit values below and therefore represents a transmission factor value $T_1...T_m$ of tinted glass reference panels, and it is thus possible to determine the optical transmission factor T of the glass panel PV by identification.

According to a particularly advantageous aspect of the method of the present invention, the reflection coefficient reference values $R_{rl}$ to $R_{rn}$ of the tinted glass reference panels are determined for shades called basic shades, corresponding to shades normally used in a standard way in the manufacture of mass-produced glass panels such as, for example, windshields for motor vehicles or aircraft.

According to another advantageous feature of the method of the invention, the reflection coefficient reference values to $R_{rl}\ R_{rn}$ for the tinted glass reference panels are included within the following limit reference values:

1 to 0.95 for a clear glass panel,
0.69 to 0.64 for a bronze-tinted glass panel,
0.45 to 0.40 for a green-tinted glass panel for radiation in the near infrared.

Of course, the ranges of the above-mentioned reflection coefficient reference values for each shade take into account inevitable variations in the values of these reflection coefficients for a considered shade, depending on manufacturing variations.

According to another advantageous aspect of the method of the invention, as shown in FIG. 1a, the incident electromagnetic radiation 1 is transmitted at low incidence and the reflected electromagnetic radiation, radiations 5 and 6, are detected symmetrically with respect to the normal N to the glass panel PV.

According to another advantageous feature of the method of the invention, the incident electromagnetic radiation can be transmitted in plane polarization, the polarization vector P being represented in FIG. 1a. The angle of incidence of the incident radiation 1 is then chosen to be equal to the Brewster angle for the glass panel considered. Of course, non-restrictively, with the incident radiation 1 being transmitted without plane polarization but at the Brewster angle for the glass panel considered, it is possible, without leaving the scope of the method of the present invention, to detect the reflected electromagnetic radiation 5, 6 in plane polarization. In both cases, it is thus possible to obtain extinguishing of the electromagnetic radiation 5 of the radiation reflected by the inlet diopter of the glass panel PV. In this case, the reflection coefficient R of the glass panel PV is related to the optical transmission factor T of this glass panel, by the new relationship:

$$R = k\left(\frac{T^2}{(1-k)^2}\right)$$

Figure 1B:
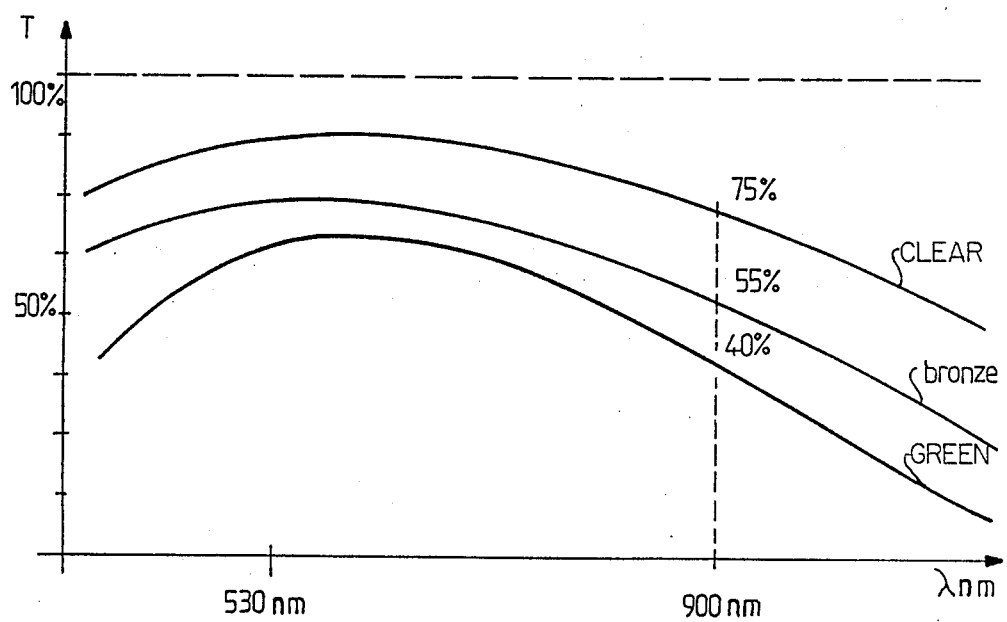
FIG. 1b is a graph representing the optical transmission factor T of a glass panel as a function of the wavelength for various shades of the glass panel, said shades being designated as basic shades.

In FIG. 1b, we have represented the principle governing the variation of the optical transmission factor T of a glass panel PV, as a function of the wavelength of the electromagnetic radiation expressed in nanometers for various basic shades of the glass panel and, in particular, for clear, bronze and green shades. For each of the basic shades considered, with the vertical axis of the graph 1b being graduated according to relative transmission values, the maximum transmission is obtained for a wavelength corresponding substantially to 530 nanometers. For a wavelength of the electromagnetic radiation corresponding to 900 nanometers, namely for a transmission of this electromagnetic radiation in the infrared zone, the transmission factors of the clear, bronze and green tinted glass panels respectively have values substantially equal to 75%, 55% and 40%. These different and unique values thus make it possible to distinguish the corresponding shade of the glass panel for a reflection coefficient R of this glass panel.

A more detailed description of a device which can be used to implement the method of the invention, described above with reference to FIGS. 1a and 1b, will now be given with reference to FIGS. 2a and 2b. According to the above-mentioned FIG. 2a, the device of the invention, making it possible to implement the above-described method, comprises, in a particular non-restrictive embodiment, circuits 10 for the transmission of an electromagnetic radiation of a determined wavelength towards the glass panel PV. The incident electromagnetic radiation is transmitted with an intensity marked $\phi_i$.

The device further comprises circuits 20 for reception of the reflected electromagnetic radiation with an intensity $\phi_r$ in the glass panel PV. Reception circuits 20 deliver a signal with an amplitude representing the intensity $\phi_r$ of the electromagnetic radiation reflected by the glass panel PV. Furthermore, as represented in FIG. 2a, there is provision for circuits 30 for the comparison of the signal representing the intensity $\phi_r$ of the reflected electromagnetic radiation, this signal, delivered by reception circuits 20, also representing the reflection coefficient $R_r$ of the glass panel PV examined, said comparison being made with respect to reflection coefficient reference values, $R_{rl}$ to $R_{rn}$, said values representing a transmission factor value $T_l$ to $T_n$ of tinted glass reference panels.

Figure 2A:
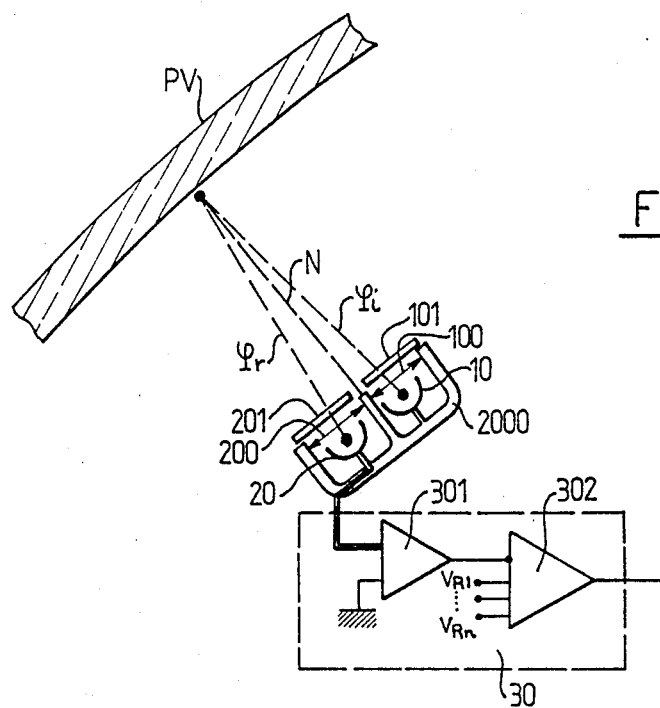
FIGS. 2a and 2b show a functional block diagram of a device providing for the implementation of the method, in accordance with the invention.

As is shown schematically in FIG. 2a, the electromagnetic radiation transmission circuits 10 advantageously comprise a light-emitting diode that transmits in the infrared radiation range and, advantageously, at a wavelength of 900 nanometers. With the transmission circuits 10, there are associated focusing means 100 and, in the case of plane polarized light transmission, a polarizing filter 101. The reception circuits 20 may consist of a photodiode for which the range of sensitivity corresponds to the emitting diode constituting the transmission circuits 10. With the reception circuits 20, there are associated suitable focusing means 200. In the same way, when there is no polarizing filter 101 at transmission, an analyzing filter 201 may be added and coupled with the focusing means 200. The entire set can thus be contained in a case marked 2000 which can be used to fix the transmission circuits and the reception circuits at a suitable distance from the glass panel PV.

Of course, the circuits 30 for the comparision of the signal representing the intensity $\phi_r$ of the reflected electromagnetic radiation and the reflection coefficient $R_r$ may advantageously comprise, as is shown schematically in FIG. 2a, a preamplifier marked 301 which receives the signal delivered directly by the electromagnetic radiation reception circuits 20. The preamplifier 301 delivers an amplified signal to a first input of a comparator 302 which receives, at several inputs, reference voltages marked $V_{rl}$ to $V_{rn}$, these reference voltages representing, of course, the corresponding values of the reflection coefficients $R_{rl}$ to $R_{nl}$ representing a value of the reflection coefficient $T_l$ to $T_n$ of tinted glass reference panels. The comparison of the amplified signal, delivered by the preamplifier 301 to the input of the comparator 302, makes it possible to determine the optical transmission factor T of the glass panel examined by identification.

As will be further noted in FIG. 2a, the electromagnetic radiation transmission circuits 10 and reception circuits 20 are slightly inclined with respect to the normal N to the glass panel PV. Preferably, the incident and reflected radiation transmission circuits 10 and reception circuits 20 are arranged symmetrically with respect to the above-mentioned normal N.

A more particularly advantageous embodiment of the comparison circuits 30 of the device of the invention, as shown in FIG. 2a, shall now be described with reference to FIG. 2b.

Figure 2B:
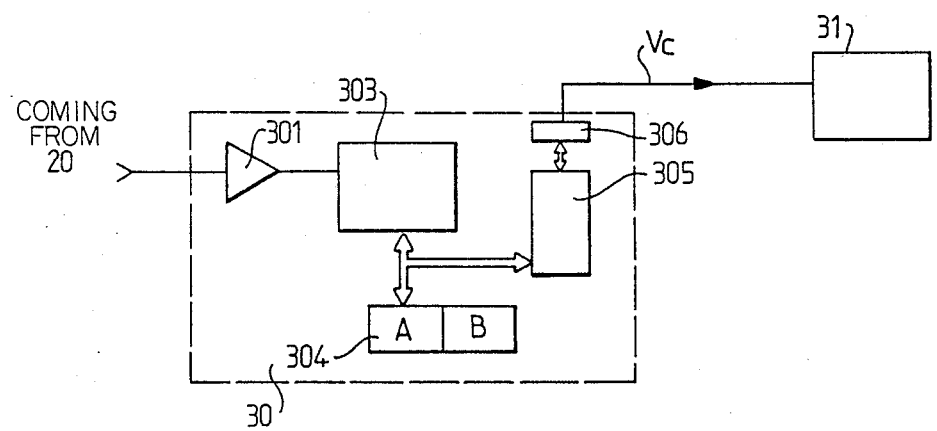

In the embodiment of FIG. 2b, the comparison circuits 30 can be used to create a signal Vc proportionate to the difference between the ratio R, representing the reflection coefficient of the glass panel PV and the nearest reference reflection coefficient value $R_{rl}$ to $R_{rn}$ within the range of reference values for each of the tinted glass reference panels. This difference is related to and represents the transmission factor T of the glass panel PV. This embodiment is more especially suited to glass panels in which the shade and, ultimately, the transmission factor varies as a function of the ambient luminosity, in a substantially continuous manner as a function of this ambient luminosity.

In this case, the signal Vc delivered by the comparison circuits 30, constitutes a continuous scale of values of the transmission factor T of the glass panel PV.

To this end, as shown in FIG. 2b, the preamplifier 301 is directly connected to a module for the sampling of the preamplified signal and for the analog/digital conversion of this signal. The sampling and analog/digital conversion module 303 is interconnected with a storage unit 304 and also with a central computing unit marked 305. The central computing unit may, advantageously, be constituted by a microprocessor such as the microprocessor used to manage the functions of the passenger space in a motor vehicle or cockpit in an aircraft According to an advantageous and non-restrictive feature, the storage unit 304 may be advantageously sub-divided into a random-access memory zone A and a read-only memory zone B. The random-access memory zone A can be used for storing the digitized values of the preamplified signal, said values representing the reflection coefficient R of the panel PV to be examined. The read-only memory zone B comprises, on the contrary, the reference reflection coefficient values $R_{rl}$ to $R_{rn}$, either representing a transmission factor value, $T_l$, $T_n$, of tinted glass reference panels or representing, for one and the same shade, different transmission factors of the glass panel PV, the absorption or transmission factor of which varies as a function of the ambient luminosity.

The central computing unit 305 then comprises a microprogrammed system which can be used to compare the measured value of the reflection coefficient R, stored in the random-access memory A of the storage unit 304, with the reference values stored in the read-only memory zone B of this same storage unit. The computing program can then be used to make any interpolation of the value of the reflection coefficient R measured with respect to two reference reflection coefficient values, $R_{rl}$ to $R_{rn}$, the difference with one or more of these values representing the transmission factor T of the glass panel PV.

Furthermore, the comparison circuits 30 also comprise an interface board 306 connected to a central computing unit 305, the interface board 306 consisting of a digital/analog conversion board delivering the above-mentioned signal Vc.

The comparator, as shown in FIG. 2b, can of course be made with components normally available in the market, and these components will not be described in greater detail.

The embodiment of the comparator and of the device of the invention, as shown in FIG. 2b and 2a in particular, may be advantageously used, the signal Vc delivered by the comparator circuits 30 making it possible to regulate the intensity of the electromagnetic radiation of a motor vehicle accessory or aircraft accessory marked 31 in FIG. 2b. In this case, of course, the glass panel PV is constituted by the windshield of the vehicle or aircraft, and the accessory 31 is constituted by a fog detector for example, attached to the windshield or glass panel PV. The signal Vc thus created by the device of the invention can be used, depending on either the shade of the windshield or its transmission factor, to control the intensity of transmission of a fog detecting device.

What is claimed is:

1. A method for determining the optical transmission factor of a tinted glass panel by reflection, said method comprising the steps of:
    transmitting an incident electromagnetic radiation of given intensity ($\phi_i$) towards one surface of the tinted glass panel for which the optical transmission factor is to be determined;
    detecting and measuring the intensity of ($\phi_r$) of the electromagnetic radiation reflected by the tinted glass panel;
    storing a number of reflection coefficient reference values ($R_{rl}...R_{rn}$) in a memory means wherein said reflection coefficient reference values ($R_{rl}...R_{rn}$) having values within the following limit reference values corresponding to the range:
    1 to 0.95 for a clear glass panel;
    0.69 to 0.64 for a bronze-tinted glass panel;
    0.45 to 0.40 for a green tinted glass panel for near infrared radiation;
    each reflection coefficient reference value being uniquely related to and representing an associated transmission factor value ($T_l...T_n$) of tinted glass reference panels;
    comparing the ratio ($R=\phi r/\phi i$) between the intensity of the reflected electromagnetic radiation measured and the intensity of the incident electromagnetic radiation with at least one reflection coefficient reference value in a number of reflection coefficient reference values ($R_{rl}...R_{rn}$), and
    determining the optical transmission factor T of the glass panel by identification by selecting the value of T corresponding to the value of R within the range of said reflection coefficient reference values.

2. A method according to claim 1 wherein the step of transmitting said incident electromagnetic radiation further includes transmitting the incident radiation at a low angle of incidence and the step of detecting the reflected electromagnetic radiation includes detecting the reflected radiation symmetrically with respect to the normal to the surface of the glass panel.

3. A method according to claim 1 wherein the step of transmitting said incident electromagnetic radiation includes transmitting the radiation in plane polarization at the Brewster angle.

4. A method according to claim 1 wherein the step of transmitting said electromagnetic radiation further includes transmitting an infrared radiation.

5. A device for determining the optical transmission factor of a tinted glass panel by reflection, said device comprising:
    means for transmitting an incident electromagnetic radiation of given intensity ($\phi_i$) towards one surface of the tinted glass panel for which the optical transmission factor is to be determined;
    means for detecting and measuring the intensity ($\phi_r$) of the electromagnetic radiation reflected by the tinted glass panel from said one surface;
    means for storing a number of reflection coefficient reference values ($R_{rl}...R_{rn}$), said reflection coefficient reference values ($R_{rl}...R_{rn}$) having values within the following limit reference values corresponding to the range:
    1 to 0.95 for a clear glass panel;
    0.69 to 0.64 for a bronze-tinted glass panel;
    0.45 to 0.40 for a green-tinted glass panel for near infrared radiation;
    each reflection coefficient reference value being uniquely related to and representing an associated transmission factor value ($T_l...T_n$) of tinted glass reference panels;
    comparing the ratio ($R=\phi r/\phi i$) between the intensity of the reflected electromagnetic radiation measured and the intensity of the incident electromagnetic radiation with at least one reflection coefficient reference value in a number of reflection coefficient reference values ($R_{rl}...R_{rn}$), and
    means responsive to said comparing means for determining the optical transmission factor T of the glass panel by identification by selecting from said reflection coefficient reference value storing means the value of T corresponding to the value of R within the range of said reflection coefficient reference values.

6. A device according to claim 5 wherein said electromagnetic radiation transmitting and detecting means are slightly inclined with respect to the normal to the surface of the glass panel.

7. A device according to claim 6 wherein said incident and reflected electromagnetic radiation transmitting and detecting means are located symmetrically with respect to the normal to the surface of the glass panel.

8. A device according to claim 7 wherein said comparing means includes means for producing a signal proportionate to the difference between the value of the ratio R representing the reflection coefficient of the glass panel and the closest value of the reference reflection coefficient ($R_{rl}...R_{rn}$) wherein the difference is related to and represents the transmission factor (T) of the glass panel.

9. A device according to claim 6 wherein said comparing means includes means for producing a signal proportionate to the difference between the value of the ratio R representing the reflection coefficient of the glass panel and the closest value of the reference reflection coefficient ($R_{rl}...R_{rn}$) wherein the difference is related to and represents the transmission factor (T) of the glass panel.

10. A device according to claim 5 wherein said comparing means includes means for producing a signal proportionate to the difference between the value of the ratio R representing the reflection coefficient of the glass panel and the closest value of the reference reflection coefficient ($R_{rl}...R_{rn}$) wherein the difference is related to and represents the transmission factor (T) of the glass panel.

11. A device according to claim 10 wherein said difference signals produced by said comparing means comprises a continuous scale of values of the transmission factor (T) of the glass panel.

12. A use of a device according to claim 5 wherein said signal produced by said comparing means controls the regulation of the intensity of the electromagnetic radiation of a motor vehicle accessory or aircraft accessory wherein the glass panel comprises the windshield of the motor vehicle or aircraft and the accessory comprises a fog detector and the intensity of the electromagnetic radiation is varied in accordance with the value of the transmission factor (T) of the windshield.

* * * * *